US00PP35731P2

(12) United States Plant Patent
Johnson

(10) Patent No.: US PP35,731 P2
(45) Date of Patent: Apr. 9, 2024

(54) DAPHNE PLANT NAMED 'MOON CANYON'

(50) Latin Name: ***Daphne* x *transatlantica***
Varietal Denomination: Moon Canyon

(71) Applicant: Joel Scott Johnson, Hillsboro, OR (US)

(72) Inventor: Joel Scott Johnson, Hillsboro, OR (US)

( * ) Notice: Subject to any disclaimer, the term of this patent is extended or adjusted under 35 U.S.C. 154(b) by 0 days.

(21) Appl. No.: 18/181,885

(22) Filed: Mar. 10, 2023

(51) Int. Cl.
*A01H 5/00* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/02; A01H 5/00
See application file for complete search history.

(56) References Cited

PUBLICATIONS https://online.flippingbook.com/view/753417629/14-15/; 2023; 4 pages.*

* cited by examiner

*Primary Examiner* — Kent L Bell
(74) *Attorney, Agent, or Firm* — Weatherly IP Solutions, LLC; James M. Weatherly

(57) ABSTRACT

A new cultivar of *Daphne* plant named 'Moon Canyon' that is characterized by its open and semi-upright plant habit, striking variegated green-centered and yellow-margined foliage in spring and cream-yellow margins from late spring and early summer, and white flowers whose orange anthers present as small orange eyes. Plants of 'Moon Canyon' are in continual bloom from late spring until fall, with peak blooming occurring in late spring and early summer. In combination, these traits set 'Moon Canyon' apart from all other varieties of *Daphne* known to the inventor.

3 Drawing Sheets

Figure 1:
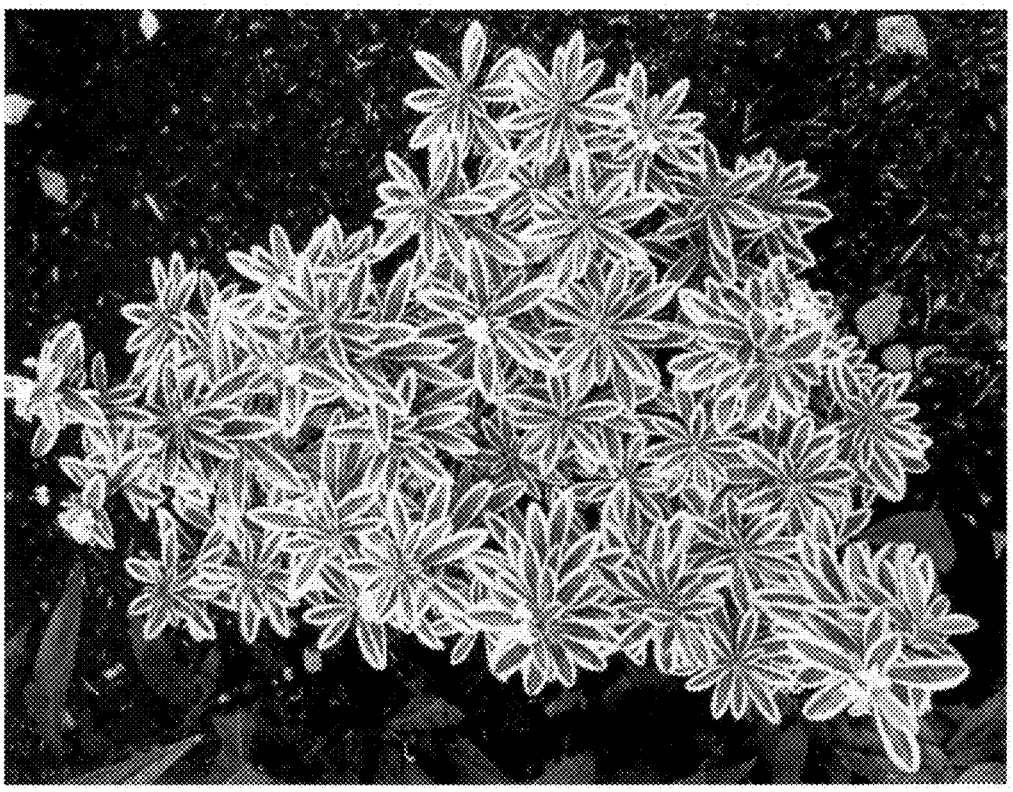

Genus and species: *Daphne* x *transatlantica*.
Variety denomination: 'Moon Canyon'.

BACKGROUND

The present disclosure relates to a new and distinct cultivar of *Daphne* plant, a shrub that is grown for use as an ornamental landscape and container plant. The new variety is known botanically as *Daphne* x *transatlantica* and will be referred to hereinafter by the cultivar name 'Moon Canyon'. *Daphne* x *transatlantica* is a newly-designated species arising from a naturally occurring cross between the low-growing species *Daphne collina* and the long blooming species *Daphne caucasica*.

'Moon Canyon' was first observed by the inventor as a naturally occurring branch sport which was growing on a single plant of *Daphne* x *transatlantica* 'Summer Ice' (unpatented) in the inventor's garden in Hillsboro, Oregon. *Daphne* x *transatlantica* 'Summer Ice' is a compact form of *Daphne* which bears variegated leaves consisting of green centers and narrow cream-yellow margins. In 2015, the inventor observed that this one plant of 'Summer Ice' had produced a naturally occurring branch mutation on which the cream-yellow leaf margins were considerably wider, extending up to 5 mm inward from the leaf edge. In 2016, in Hillsboro, Oregon, the inventor took and rooted a small number of softwood cuttings in order to establish the variegated form on its own roots, to evaluate its stability, and to increase numbers for commercial introduction.

The inventor has determined from repeated cycles of asexual reproduction that 'Moon Canyon' is a stable cultivar which reproduces and remains true-to-type.

SUMMARY

The following traits have been repeatedly observed and represent the distinguishing characteristics of 'Moon Canyon'. 'Moon Canyon' has not been tested under all possible conditions and phenotypic differences may be observed with variations in environmental, climatic, and cultural conditions, without however, any variance in genotype.

1. 'Moon Canyon' is slow growing and exhibits an open semi-upright plant habit.
2. The leaves of 'Moon Canyon' are variegated, with green centers and broad contrasting yellow margins in the spring and early summer, and cream-yellow margins from mid-summer onwards.
3. The yellow spring margins extend around the entire leaf, including at the leaf apex.
4. The flower buds of 'Moon Canyon' are light pink-purple in color.
5. The open flowers of 'Moon Canyon' are white in color and bear orange-colored anthers which present as a central orange eye.
6. Plants of 'Moon Canyon' are in continual bloom from spring until fall, with peak blooming in late spring and early summer.

DESCRIPTION OF THE PHOTOGRAPHS

The accompanying color photographs illustrate the overall appearance of the new *Daphne* cultivar 'Moon Canyon' showing the colors as true as it is reasonably possible to obtain in colored reproductions of this type. Colors in the photographs may differ from the color values cited in the detailed botanical description, which accurately describes the observed colors of 'Moon Canyon'.

FIG. 1 depicts an entire plant of 'Moon Canyon' in bud and flower in early summer. The illustrated plant is the inventor's original plant established on its own roots after removal of the mutated branch from the parent variety 'Summer Ice'. This plant is low growing and very well branched having been used for multiple propagations to increase quantities.

Figure 2:
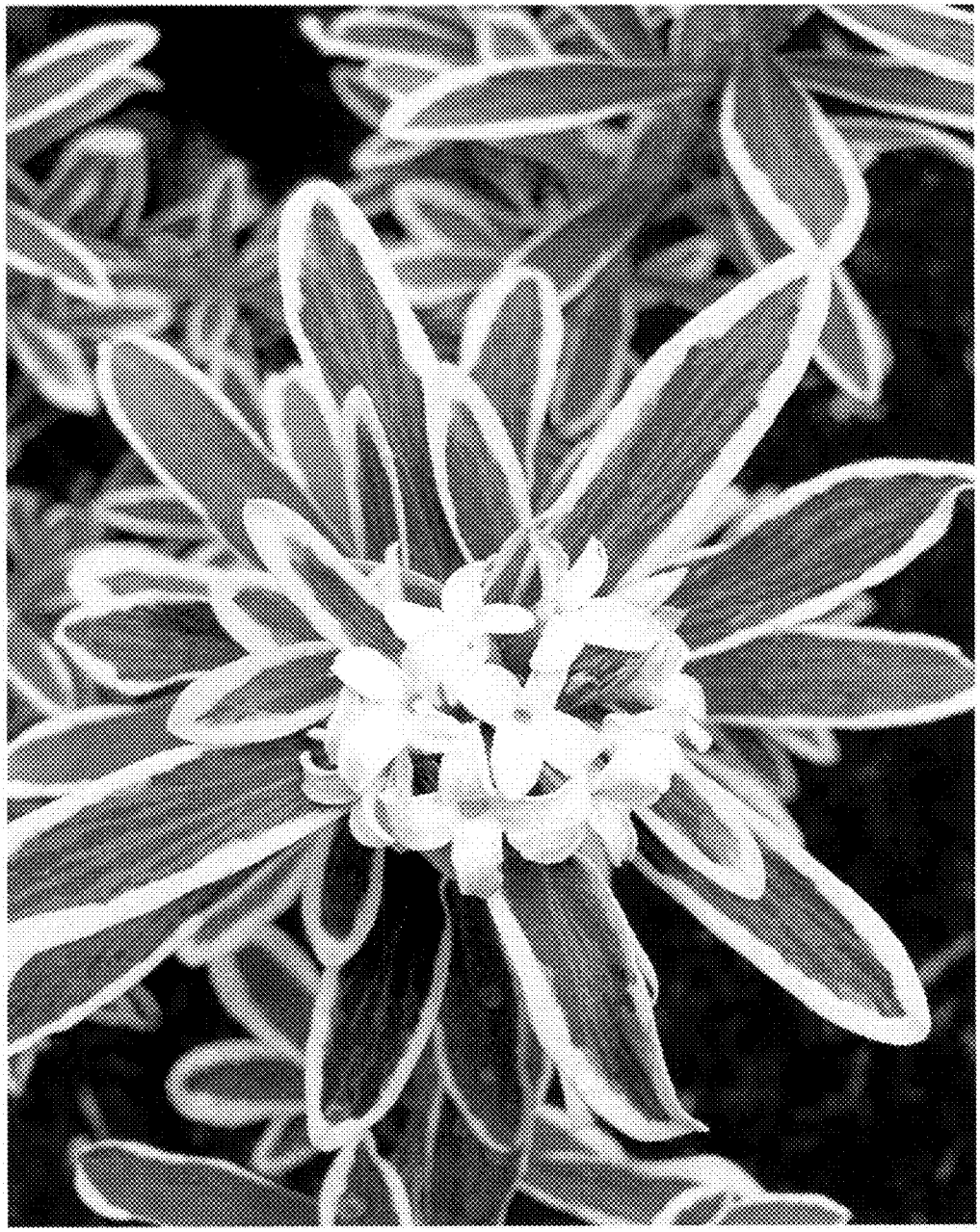

FIG. 2 presents a close-up view of the leaves and flowers of 'Moon Canyon' in mid-summer. The photograph used in FIG. 2 was taken in August in Santa Barbara, California from a two-year-old plant grown outdoors in a 2-gallon container, with one pinch after initial cutting establishment.

Figure 3:
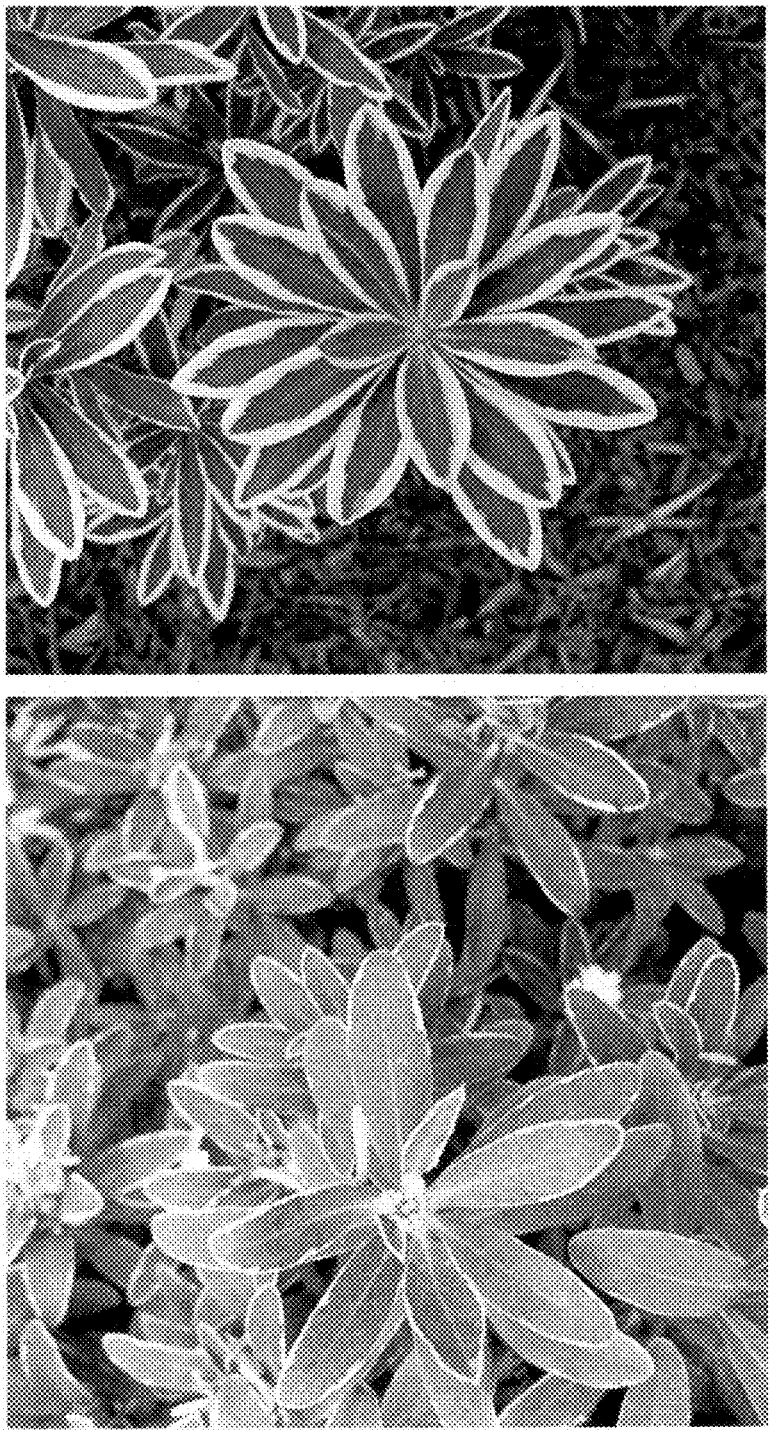

FIG. 3 presents a comparison of 'Moon Canyon' (shown above) with its sport parent variety 'Summer Ice' (shown below). FIG. 3 was prepared by the inventor using plants of the respective varieties which were growing in ground in the inventor's garden.

DESCRIPTION OF THE NEW VARIETY

The following is a detailed description of the new *Daphne* cultivar named 'Moon Canyon'. Data was collected in Santa Barbara, California from a plant grown out-of-doors in a 2-gallon container. Phenotypic differences may be observed with variations in environmental, climatic, and cultural conditions, without however, any difference in genotype. Color determinations are in accordance with the 2007 edition of The Royal Horticultural Society Colour Chart except where general color terms of ordinary dictionary significance are used.

Classification:

*Family.*—Thymelaeaceae.

*Genus.*—*Daphne.*

*Species.*—x *transatlantica*. (*D. collina* x *D. caucasica*).

*Denomination.*—'Moon Canyon'.

*Common name.*—*Daphne.*

Plant:

*Plant type.*—Shrub.

*Plant use.*—For container and landscape.

*Plant parentage.*—*Daphne* x *transatlantica* 'Moon Canyon' occurred as a naturally occurring branch mutation found growing on a single plant of *Daphne* x *transatlantica* 'Summer Ice'.

*Plant vigor.*—Low, relatively slow to root and to grow to saleable size.

*Plant shape.*—Rounded.

*Branching habit.*—Open.

*Dimensions after* 2 *years.*—30 cm-40 cm in height and 40 cm. in width.

*Plant hardiness.*—USDA Zone 5.

*Bloom season.*—Flowers are borne throughout late spring until fall. Peak flowering occurs in late spring and early summer.

Propagation, growing:

*Asexual propagation method.*—Semi-ripe cuttings taken from mid-May onwards.

*Growth habit.*—Semi-upright.

*Growing considerations.*—Maintain healthy root system by avoiding extremes of moisture and root zone temperature and practice mulching of plants in the landscape.

*Roots.*—Slow to develop, fine, light brown in color.

*Sunlight.*—Full sun or partial shade. Afternoon shade is beneficial in hot summers.

*Soil.*—Plants grow well in acidic or slightly alkaline well-draining soils or proprietary growing medium.

*Time to initiate roots.*—6-8 weeks to develop roots on an initial cutting.

*Crop time.*—13-14 months to fill out a 1-gallon container. Additional growing seasons are required to fill out a 2-gallon or larger container.

*Special considerations.*—All parts of *Daphne* plants are poisonous if ingested.

*Pest susceptibility.*—None specific to the variety.

*Disease susceptibility.*—*Botrytis* may arise when plants are exposed to prolonged wet conditions.

Stem (below first pinch or stop), branches:

*Stem shape.*—Terete.

*Stem dimensions.*—10 cm-12 cm in length, 5 mm-6 mm in diameter.

*Stem surface pubescent, hair color.*—155B.

*Stem color.*—144A.

*Lenticels.*—Present around the stem, approximately two lenticels per 1 cm of stem length, narrowly elliptic in shape, length 5 mm, width 1.5 mm, color 162D except center 147A.

*Branches.*—

*Quantity.*—4 primary branches, 6-10 secondary branches.

*Branch stem shape.*—Terete.

*Branch stem color* (*lower, older growth*).—187B with longitudinal striations 196A.

*Branch stem color* (*upper, newer growth*).—199C.

*Branch stem surface.*—Smooth, lightly puberulent.

*Branch stem length.*—15 cm-18 cm.

*Branch stem diameter.*—3 mm-4 mm.

*Internode distance.*—1.5 cm-3.5 cm.

Foliage:

*Foliage type.*—Semi-evergreen.

*Leaf attachment.*—Sessile.

*Leaf arrangement.*—Alternate.

*Leaf division.*—Simple.

*Leaf shape.*—Narrowly elliptic.

*Leaf texture.*—Smooth, glabrous.

*Leaf appearance* (*adaxial surface*).—Semi-glossy.

*Leaf appearance* (*abaxial surface*).—Matte.

*Leaf length.*—45 mm.

*Leaf width.*—13 mm.

*Leaf variegation, description.*—Both leaf surfaces contain a green central section which lies within broad cream (spring time) or cream-yellow (after spring) marginal bands. The marginal bands extend around the entire perimeter of the leaf, including the apex, and for a distance between 2 mm and 5 mm inward from the leaf edge.

*Leaf color* (*spring growth, both surfaces*).—Central section: Ranges between and including 137C and 137D, with striations (not veins) 191C. Marginal band: 4B.

*Leaf color* (*mid-summer and later growth, both surfaces*).—Central section: Ranges between and including 138A and 138B, with striations (not veins) 191C. Marginal band: 2D.

*Leaf apex.*—Rounded, occasionally mucronate, tip 0.5 mm-1.0 mm in length and width.

*Leaf base.*—Attenuate.

*Leaf margin.*—Smooth, entire.

*Venation.*—Not apparent on either leaf surface.

Inflorescence:

*Inflorescence type.*—Terminal or axillary head.

*Inflorescence dimensions.*—4.5 cm in width, 2.5 cm in overall height.

*Flower description.*—Flowers are apetalous and are formed by four petaloid sepals whose fused edges form the corolla tube and whose free lobes imitate petals.

*Flower quantity.*—16-20 flowers per inflorescence.

*Flower bloom time.*—Peak flowering in April and May, continues through summer months until November.

*Flower shape.*—Salverform.

*Flower dimensions.*—15 mm in diameter and 12 mm in height.

*Flower attachment* (*buds, flowers*).—Very short pedicels or sessile.

*Pedicels* (*where present*).—Up to 2 mm in length, 0.75 mm in diameter, puberulent, color 182C.

*Bud arrangement.*—Tight axillary clusters.

*Bud color* (*in tight bud*).—Light red-purple 72D.

*Bud shape.*—Scepter-shaped (cylindrical sepal tube, near-globular unopened sepal lobes).

*Bud dimensions.*—3 mm-4 mm in length, including tube; 1 mm in diameter (tube), 2.5 mm in diameter (unopened sepal lobes).

*Bud surface.*—Puberulent.

*Bud apex.*—Rounded.

*Bud base.*—Obtuse.

*Corolla description* (*flowers open*).—

*Corolla shape.*—Tubular, formed by four fused sepals.

*Corolla color.*—182C.

*Corolla dimensions.*—3 mm. in length and 1 mm in diameter.

*Corolla surface* (*outer*).—Pubescent.

*Corolla tube surface* (*inner*).—Glabrous.

*Sepal lobes.*—4 in number, free, rotate.

*Sepal lobe surface* (*both surfaces*).—Glabrous.

*Sepal lobe shape.*—Oblong, downwardly recurved.

*Sepal lobe color* (*adaxial surface*).—Initially pale pink N155D, becoming NN155D.

*Sepal lobe color* (*abaxial surface*).—NN155D.

*Sepal lobe dimensions.*—12 mm-15 mm in length, 5 mm-6 mm in width.

*Sepal lobe apex.*—Rounded.

*Sepal lobe base.*—Truncate (sepals becomes fused).

*Sepal lobe margin.*—Smooth, entire, glabrous.

*Flower fragrance.*—Intense perfume fragrance.

*Lastingness of flowers.*—Up to 7 days in spring and fall, and 5 days in summer.

*Persistence of flowers.*—Persistent.

Reproductive organs:

*Stamens.*—8 in two whorls, lower and upper, of 4 stamens each.

*Stamen attachment.*—Adnate to interior of corolla tube.

*Stamen length.*—1 mm (lower whorl), 2 mm (upper whorl). Anthers on upper stamens borne at mouth of corolla tube, base of lobes.

*Stamen color.*—155B.

*Anthers.*—Ovoid, 0.5 mm in length and width.

*Anther color.*—25A.

*Pollen.*—Slight, color 25A.

*Pistil, style.*—Absent.

*Stigma attachment.*—Sessile (style absent).

*Stigma shape.*—Orbicular.

*Stigma surface.*—Glabrous.

*Stigma color.*—155A.

*Stigma dimensions.*—0.50 mm in diameter.

*Ovary.*—Superior, globose, 1.5 mm in diameter, color 150D.

Fruit and seed: None observed.

COMPARISON WITH PARENT VARIETY

'Moon Canyon' is distinguished from its sport parent variety *Daphne* 'Summer Ice' by the extent of the variegation which is exhibited by both varieties, Whereas the marginal band of 'Summer Ice' is narrow, less than 1 mm in width, and not present around the entire leaf margin, the marginal band of the instant variety 'Moon Canyon' is 2 mm to 5 mm in width and is present entirely around the perimeter of the leaf. In addition, the color of the marginal band of 'Moon Canyon' is cream-yellow, whereas the color of the marginal band of 'Summer Ice' is white.

COMPARISON WITH KNOWN VARIETIES

Except for 'Summer Ice' as above, no other variegated varieties of *Daphne* x *transatlantica* are known to the inventor. The variety *Daphne* x *transatlantica* 'BLAFRA' (U.S. Plant Pat. No. 18,361 is non-variegated. The following varieties of *Daphne* are all variegated but are varieties of the species *Daphne burkwoodii* or *Daphne oroda:*

*Daphne burkwoodii* 'Carol Mackie' (unpatented).

*Daphne burkwoodii* 'MonMkie' (U.S. Plant Pat. No. 29,000).

*Daphne burkwoodii* 'Moonlight Sonata' (U.S. Plant Pat. No. 26,654).

*Daphne burkwoodii* 'Briggs Moonlight' (unpatented).

*Daphne odora* 'HEWREB' (U.S. Plant Pat. No. 18,368).

Whereas plants of the species *Daphne burkwoodii* and *Daphne odora* bear pink or purple flowers, varieties of plants of the species *Daphne* x *transatlantica*, known to the inventor, including 'Moon Canyon', bear white flowers. In addition, plants of 'Moonlight Sonata' and 'Briggs Moonlight' exhibit reverse leaf variegation, namely yellow centers and green margins.

I claim:

1. A new and distinct cultivar of *Daphne* Plant Named 'Moon Canyon' as described and illustrated herein.

* * * * *